United States Patent
Leonard et al.

(10) Patent No.: US 8,596,380 B2
(45) Date of Patent: *Dec. 3, 2013

(54) SYSTEM AND METHOD FOR ASSESSING HYDROGEN SULFIDE IN A HYDROCARBON EXTRACTION WELL IN SITU IN AN ONGOING MANNER

(75) Inventors: Benjamin Leonard, Harris, TX (US); Gerard Simon, Harris, TX (US); Gregory Russ Goddard, Eugene, OR (US)

(73) Assignees: Chevron U.S.A. Inc., San Ramon, CA (US); Los Alamos National Security, LLC, Los Alamos, NM (US)

( * ) Notice: Subject to any disclaimer, the term of this patent is extended or adjusted under 35 U.S.C. 154(b) by 408 days.

This patent is subject to a terminal disclaimer.

(21) Appl. No.: 12/958,054

(22) Filed: Dec. 1, 2010

(65) Prior Publication Data

US 2012/0138364 A1     Jun. 7, 2012

(51) Int. Cl.
*E21B 47/00* (2012.01)

(52) U.S. Cl.
USPC .......................... 175/40; 166/66; 166/250.01

(58) Field of Classification Search
USPC ........... 166/66, 250.01; 175/40; 324/324, 325
See application file for complete search history.

(56) References Cited

U.S. PATENT DOCUMENTS

| | | | | |
|---|---|---|---|---|
| 3,490,480 A | * | 1/1970 | Parsons | 137/93 |
| 4,468,611 A | * | 8/1984 | Tward | 324/673 |
| 4,473,114 A | * | 9/1984 | Bell et al. | 166/248 |
| 5,832,411 A | | 11/1998 | Schatzmann et al. | |
| 6,740,216 B2 | * | 5/2004 | Diakonov et al. | 204/418 |
| 6,939,717 B2 | * | 9/2005 | Jiang et al. | 436/121 |

FOREIGN PATENT DOCUMENTS

| | | |
|---|---|---|
| EP | 0260005 A2 | 3/1988 |
| WO | 87/01204 A1 | 2/1987 |

OTHER PUBLICATIONS

International Search Report and Written Opinion for PCT International Patent Application No. PCT/US2011/062567, mailed Mar. 26, 2012.

* cited by examiner

*Primary Examiner* — Nicole Coy
(74) *Attorney, Agent, or Firm* — Pillsbury Winthrop Shaw Pittman LLP

(57) ABSTRACT

The level of hydrogen sulfide in drilling fluid within a well formed in the Earth is assessed in an ongoing and/or in situ manner. The well may be constructed for the removal of hydrocarbons from the Earth. The assessment of hydrogen sulfide level may be provided in an ongoing manner such that real time, or near real time, fluctuations in hydrogen sulfide levels in the drilling fluid within the well may be conveyed to users. This may provide various advantages over systems in which drilling fluid must be extracted and separately tested for hydrogen sulfide content, and/or in which assessments of hydrogen sulfide level require time for performance.

14 Claims, 2 Drawing Sheets

SYSTEM AND METHOD FOR ASSESSING HYDROGEN SULFIDE IN A HYDROCARBON EXTRACTION WELL IN SITU IN AN ONGOING MANNER

FIELD OF THE INVENTION

The invention relates to the ongoing, in situ monitoring of hydrogen sulfide levels in a well for the extraction of hydrocarbons.

BACKGROUND OF THE INVENTION

In a well used for hydrocarbon extraction, substances may be present that inhibit operation of the well. These substances may be bound up in strata being excavated to form the well and/or the substances may migrate from adjacent strata. One example of such a substance is hydrogen sulfide. Conventional mechanisms for determining a level of hydrogen sulfide in drilling fluid within a well require extraction of drilling fluid for measurement, require a relatively length measurement process, are labor intensive, and/or suffer from other drawbacks.

SUMMARY

One aspect of this disclosure relates to a measurement system configured to assess hydrogen sulfide ($H_2S$) concentration within drilling fluid, the drilling fluid being part of a drilling system configured to drill a wellbore in the Earth. In one embodiment, the measurement system comprises an intermittent assessment subsystem and an ongoing assessment subsystem. The intermittent assessment subsystem is configured to quantitatively determine hydrogen sulfide concentration in the drilling fluid on an intermittent basis. The ongoing assessment subsystem is configured to qualitatively assess changes in hydrogen sulfide concentration in the drilling fluid in situ and on an ongoing basis. The ongoing assessment subsystem comprises electrical conductors, a signal generator, and a processor. The electrical conductors are in direct contact with drilling fluid within the drilling system. The signal generator is configured to apply an electric potential between the electrical conductors such that an electric current runs between the electrical conductors through the drilling fluid. The processor is configured to measure an electrical property of the drilling fluid based on a parameter of the electric current, wherein values for the electrical property are a function of hydrogen sulfide concentration in the drilling fluid, and wherein the ongoing assessment of changes in hydrogen sulfide concentration by the ongoing assessment subsystem is calibrated with the quantitative determination of hydrogen sulfide concentration provided intermittently by the intermittent assessment subsystem, so as to provide for a qualitative, in situ, continuous monitoring of hydrogen sulfide in the drilling fluid.

Another aspect of this disclosure relates to a method of assessing, in situ, hydrogen sulfide ($H_2S$) concentration within drilling fluid in a drilling system configured to drill a wellbore in the Earth. In one embodiment, the method comprising the steps of a) applying an electric potential between electrical conductors disposed in direct contact with the drilling fluid in the drilling system such that an electric current runs between the electrical conductors through the drilling fluid; b) determining a value of an electrical property of the drilling fluid based on a parameter of the electric current running through the drilling fluid, wherein the value of the electrical property is a function of hydrogen sulfide concentration in the drilling fluid; c) quantitatively measuring hydrogen sulfide concentration in the drilling fluid; d) correlating the quantitative measurement with the value of the electrical property of the drilling fluid determined at (b); e) calibrating an assessment of hydrogen sulfide concentration in the drilling fluid that is based on determined values of the electrical property of the drilling fluid, wherein the calibration is based on the correlation performed at (d); and d) qualitatively assessing, in situ and on ongoing basis, hydrogen sulfide concentration in the drilling fluid based on ongoing determinations of the value of the electrical property of the drilling fluid.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
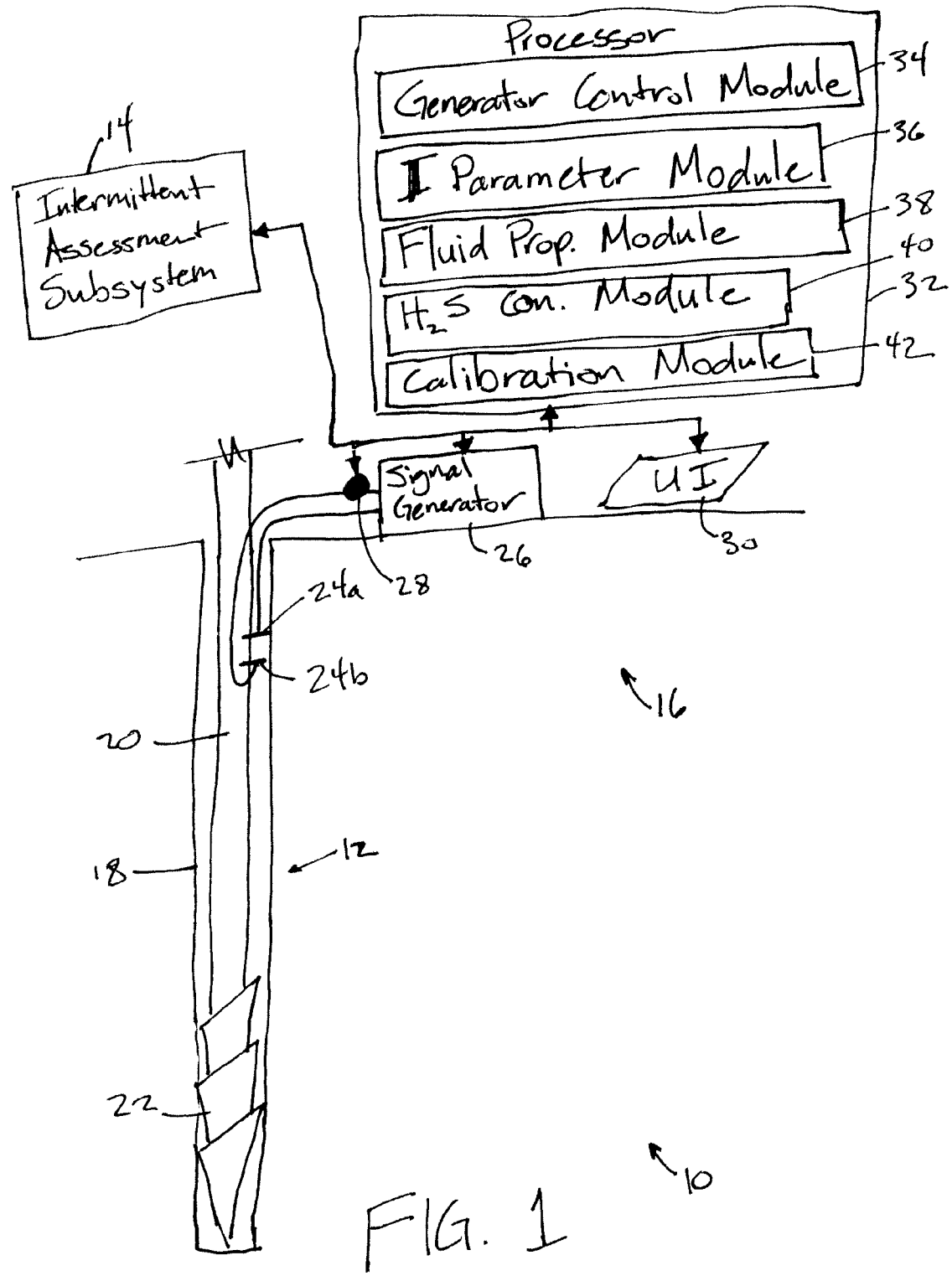
FIG. 1 illustrates a system configured to assess the level of hydrogen sulfide in drilling fluid within a well, in accordance with one or more embodiments of the invention.

FIG. 1 illustrates a system 10 configured to assess the level of hydrogen sulfide in drilling fluid within a well 12 formed in the Earth. The well 12 may be constructed for the removal of hydrocarbons from the Earth. The system 10 is configured to provide the assessment of hydrogen sulfide in an ongoing manner such that real time, or near real time, fluctuations in hydrogen sulfide levels in the drilling fluid within well 12 may be conveyed. System 10 is further configured to assess hydrogen sulfide levels of drilling fluid in situ, and/or for drilling fluid that is water-based. This may provide various advantages over systems in which drilling fluid must be extracted and separately tested for hydrogen sulfide content, and/or in which assessments of hydrogen sulfide level require time for performance. The system 10 includes one or more of an intermittent assessment subsystem 14, an ongoing assessment subsystem 16, and/or other components.

The well 12 is constructed within a casing 18, with a conduit 20 extending down into well 12 within casing 18. The conduit 20 extends down into well 12 within casing 18, and is part of or and/or carried by a drill pipe that extends toward the surface from a drill bit 22 engaged in deepening (or widening a previously drilled section of) well 12. The conduit 20 is configured to carry drilling fluid from a pump (not shown) into well 12 under pressure. Fluid dispensed from conduit 20 into well 12 stabilizes well 12, removes cuttings, lubricates and/or cleans drill bit 22, and/or serves other purposes within well 12. As drilling continues, substances in the strata around well 12 may migrate into the drilling fluid. Such substances may include substances in strata excavated by drill bit 22, gas and/or liquids that migrate into well 12 through casing 18, and/or other substances. Some of these substances, such as hydrogen sulfide, may be undesirable.

The intermittent assessment subsystem 14 is configured to measure the hydrogen sulfide level of drilling fluid. The measurement taken by intermittent assessment subsystem 14 may be direct and/or quantitative. The measurement taken by intermittent assessment subsystem 14 may have a relatively high level of precision, accuracy, and/or reliability. The intermittent assessment subsystem 14 may be configured to measure the hydrogen sulfide level of drilling fluid from well 12 on an intermittent basis. The intermittent measurements may be periodic, made based upon user input and/or interaction, and/or made at other intermittent times. In one embodiment, the measurement made by intermittent assessment subsystem 14 requires a portion of the drilling fluid within well 12 to be extracted from well 12 for measurement. In this embodiment, well 12 may include drilling fluid recovery module (not shown) configured to extract or recover drilling fluid for well 12 for measurement. In one embodiment, the measurement made by intermittent assessment subsystem 14 is not instantaneous (or nearly instantaneous). In this embodiment, the measurement made by intermittent assessment subsystem 14 takes time to complete. The intermittent assessment subsystem 14 may include, for example, a Garrett gas train, Gas Chromatography, Gas Chromatography-Mass Spectrometry, Optical Spectroscopies such as Raman Spectroscopy, and/or other measurement systems.

The ongoing assessment subsystem 16 is configured to provide an ongoing and/or in situ assessment of the hydrogen sulfide level of drilling fluid within well 12. The assessment provided by ongoing assessment subsystem 16 may be indirect and/or qualitative. The assessment provided by ongoing assessment subsystem 16 may be less reliable, precise, and/or accurate than the measurements made by intermittent assessment subsystem 14. As such, the assessment provided by ongoing assessment subsystem 16 may be calibrated based on measurements made by intermittent assessment subsystem 14. The ongoing assessment subsystem 16 includes one or more of electrical conductors 24 (illustrated as a first conductor 24a and a second conductor 24b), a signal generator 26, a sensor 28, a user interface 30, a processor 32, and/or other components.

It will be appreciated that the use of the term "ongoing" herein does not preclude determination of periodic samples that indicate the hydrogen sulfide level of the drilling fluid. Instead, the term "ongoing" may mean that the sampling rate of such determinations is great enough that ongoing assessment subsystem 16 provides an indication of the hydrogen sulfide level in a continuous (or substantially continuous) manner. For example, the sampling rate may include any rate between a substantially continuous sampling to about 10 samples per hour.

The electrical conductors 24 are configured to be disposed in the drilling fluid within well 12. During assessment of the hydrogen sulfide level within the drilling fluid, a current runs through the drilling fluid between electrical conductors 24 (as is discussed herein). In one embodiment, electrical conductors 24 are arranged in a coaxial configuration with first conductor 24a forming the inner conductor and second conductor 24b forming the outer conductor encasing the inner conductor.

The signal generator 26 is configured to apply an electric potential between electrical conductors 24. The electric potential is applied to electrical conductors 24 such that an electric current runs between electrical conductors 24 through the drilling fluid. To apply the electric potential to electrical conductors 24, signal generator 26 is in operative communication with electrical conductors 24 (e.g., via electric leads). The signal generator 26 may be disposed within well 12, or outside of well 12 (e.g., at or near the surface).

The sensor 28 is configured to detect one or more parameters of the electric current through the drilling fluid between electrical conductors 24. The one or more parameters may include one or more of current (rate of flow of electric charge), current phase, current periodicity, and/or other parameters. In one embodiment, sensor 28 is in operative communication with the electric circuit formed between electrical conductors 24 and signal generator 26. By monitoring electric current in this circuit between, for example, one of electrical conductors 24 and signal generator 26, sensor 28 can detect one or more parameters of the electric current within the drilling fluid between electrical conductors 24. In one embodiment, sensor 28 includes an optical sensor configured to generate output signals conveying information related to the dielectric properties of the drilling fluid (e.g., a polarimeter). Although sensor 28 is illustrated in FIG. 1 as an individual entity, it will be appreciated that this is not intended to be limiting. In one embodiment, sensor 28 includes a plurality of individual sensors that monitor one or more parameters of the electric current through the drilling fluid between electrical conductors 24.

User interface 30 is configured to provide an interface between ongoing assessment subsystem 16 and users through which users provide information to and receive information from ongoing assessment subsystem 16. This enables data, results, and/or instructions and any other communicable items, collectively referred to as "information," to be communicated between the users and ongoing assessment subsystem 16. Examples of interface devices suitable for inclusion in user interface 30 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 30. For example, the present invention contemplates that user interface 30 may be integrated with a removable storage interface configured to receive removable electronic storage media. In this example, information may be loaded into, and/or uploaded to, ongoing assessment subsystem 16 from removable storage (e.g., a smart card, a flash drive, a removable disk, etc.) that enables the user(s) to customize the implementation of ongoing assessment subsystem 16. Other exemplary input devices and techniques adapted for use with ongoing assessment subsystem 16 as user interface 30 include, but are not limited to, an RS-232 port, RF link, an IR link, modem (telephone, cable or other). In short, any technique for communicating information with ongoing assessment subsystem 16 is contemplated by the present invention as user interface 30.

Processor 32 is configured to provide information processing capabilities in ongoing assessment subsystem 16. As such, processor 32 may include one or more of a digital processor, an analog processor, a digital circuit designed to process information, an analog circuit designed to process information, a state machine, and/or other mechanisms for electronically processing information. Although processor 32 is shown in FIG. 1 as a single entity, this is for illustrative purposes only. In some implementations, processor 32 may include a plurality of processing units. These processing units may be physically located within the same device, or processor 32 may represent processing functionality of a plurality of devices operating in coordination.

As is shown in FIG. 1, processor 32 may be configured to execute one or more computer program modules. The one or more computer program modules may include one or more of a generator control module 34, a current parameter module 36, a fluid property module 38, a hydrogen sulfide concentration module 40, a calibration module 42, and/or other modules. Processor 32 may be configured to execute modules 34, 36, 38, 40, and/or 42 by software; hardware; firmware; some combination of software, hardware, and/or firmware; and/or other mechanisms for configuring processing capabilities on processor 32.

It should be appreciated that although modules 34, 36, 38, 40, and 42 are illustrated in FIG. 1 as being co-located within a single processing unit, in implementations in which processor 32 includes multiple processing units, one or more of modules 34, 36, 38, 40, and/or 42 may be located remotely from the other modules. The description of the functionality provided by the different modules 34, 36, 38, 40, and/or 42 described below is for illustrative purposes, and is not intended to be limiting, as any of modules 34, 36, 38, 40, and/or 42 may provide more or less functionality than is described. For example, one or more of modules 34, 36, 38, 40, and/or 42 may be eliminated, and some or all of its functionality may be provided by other ones of modules 34, 36, 38, 40, and/or 42. As another example, processor 32 may be configured to execute one or more additional modules that may perform some or all of the functionality attributed below to one of modules 34, 36, 38, 40, and/or 42.

The generator control module 34 is configured to control signal generator 26 in the application of the electric potential between electrical conductors 24. This may include controlling one or more of the frequency, the phase, the wave shape, amplitude, the polarity, and/or other parameters of the electric potential.

The presence and amount of hydrogen sulfide present in the drilling fluid causes one or more electrically significant phenomena that will impact various aspects of the electrical circuit formed by signal generator 26, electrical conductors 24, and the drilling fluid. For example, the electrically significant phenomena may include one or more of chemical reaction of hydrogen sulfide with lime, dissolving hydrogen sulfide, gas bubbles within the drilling fluid caused by hydrogen sulfide, and/or other phenomena within the drilling fluid caused by the presence of hydrogen sulfide that impact the electric current between electrical conductors 24.

The generator control module 34 is configured to control signal generator 26 such that one or more parameters of the electric potential applied to electrical conductors 24 is set at a level at which the impact of one or more of the electrically significant phenomena will be enhanced. For example, one or more of the electrically significant phenomena may have specific frequency ranges within which their impact on the electric current is more appreciable. These frequency ranges may be resonant frequency ranges determinable by dielectric spectroscopy. As a non-limiting example, the frequency of the potential may be set by generator control module 34 at between about 50 MHz and about 80 MHz, and/or other frequencies. As a non-limiting example, the amplitude of the potential may be about 100 mV, and/or other amplitudes.

The current parameter module 36 is configured to determine one or more parameters of the current induced within the drilling fluid between electrical conductors 24. This determination may be based on signals received from sensor 28. The one or more parameters may include one or more of frequency, phase, wave shape, amplitude, and/or other parameters of the current induced between electrical conductors 24.

The fluid property module 38 is configured to monitor one or more electrical properties of the drilling fluid. This may include determining values of the one or more electrical properties of the drilling fluid based on one or more parameters of the potential applied to electrical conductors 24 and/or one or more parameters of the electric current induced within the drilling fluid between electrical conductors 24. The one or more electrical properties of the drilling fluid may include, for example, reflectance, resistance, susceptibility, impedance, permittivity, admittance, real and imaginary terms, S-parameters, and/or other properties. By way of non-limiting example, based on a phase difference between the potential and the current, the value of reflectance of the drilling fluid may be determined.

The hydrogen sulfide concentration module 40 may be configured to assess the level of hydrogen sulfide in the drilling fluid based on the property or properties monitored by fluid property module 38, the parameters monitored by current parameter module 36, and/or other variables. Assessing the level of hydrogen sulfide may include determining or estimating the level of hydrogen sulfide, determining whether a threshold level of hydrogen sulfide has been reached, assessing changes in the level of hydrogen sulfide in the drilling fluid, and/or otherwise assessing the level of hydrogen sulfide. The assessment of the level of hydrogen sulfide may be made by hydrogen sulfide concentration module 40 at or near the sampling rate at which the values of the one or more electrical properties are determined. The hydrogen sulfide concentration module 40 may be configured to present assessments of the level of hydrogen sulfide to users via, for example, user interface 30.

Assessment of the level of hydrogen sulfide in the drilling fluid based on the property or properties monitored by fluid property module 38 may be based solely on the property(ies), or may be based on other parameters impacting electrical properties of the drilling fluid. For example, assessment of the level of hydrogen sulfide in the drilling fluid may be adjusted for current temperature, current pressure, and/or other the current state of other parameters in the drilling fluid at or near electrical conductors 24. The current state of temperature, pressure, and/or other parameters in the drilling fluid may be determined based on output of other sensors (not shown) within well 12.

In one embodiment, hydrogen sulfide concentration module 40 is configured to make a determination of the level of hydrogen sulfide as a function of the values of one or more of the electrical properties determined by fluid property module 38. The hydrogen sulfide concentration module 40 may present the determined level of hydrogen sulfide to users via user interface 30. Presentation of the determined level may include providing a numeric indication of the determination, a descriptive presentation (e.g., low, moderate, high, etc.), illumination of one or more indicator lights (e.g., green for low, yellow for moderate, red for high, etc.), and/or other mechanisms for presenting the determined level of hydrogen sulfide.

In one embodiment, hydrogen sulfide concentration module 40 is configured to compare a metric related to the level of hydrogen sulfide with a threshold. The metric may include the values of an electric property determined by fluid property module 38, an estimate of the level of hydrogen sulfide derived from the values of the electrical property(ies) determined by fluid property module 38, and/or other metrics related to the level of hydrogen sulfide. Responsive to the metric breaching the threshold, hydrogen sulfide concentration module 40 may be configured to take one or more of a variety of actions. For example, hydrogen sulfide concentration module 40 may activate an alarm signal to the users via user interface 30, hydrogen sulfide concentration module 40 may indicate a different level of hydrogen sulfide to the users via user interface 30, hydrogen sulfide concentration module 40 may automatically shut down operations at well 12 (e.g., drilling operations, extraction operations, and/or other operations), and/or may take other action.

The calibration module 42 is configured to calibrate the assessment of hydrogen sulfide levels by hydrogen sulfide concentration module 40. The calibration module 42 is configured to do this by correlating values of the electric property(ies) with contemporaneous measurements of hydrogen sulfide concentration taken by intermittent assessment subsystem 14. The calibration may involve a single correlation between the most recent measurement taken by intermittent assessment subsystem 14 and a temporally corresponding set of determinations made by one or more of current parameter module 36, fluid property module 38, and/or hydrogen sulfide concentration module 40. The calibration may account for previous measurements and corresponding determinations by modules 36, 38, and/or 40 (e.g., older measurements and determinations may be given less weight). Calibration by calibration module 42 may include adjusting a function that determines a level of hydrogen sulfide (or a corresponding metric) as a function of a parameter or property monitored by current parameter module 36 and/or fluid property module 38, adjusting a threshold used by hydrogen sulfide concentration module 40 in assessing the level of hydrogen sulfide (e.g., an alarm threshold), adjusting a sensitivity to changes in one or more of the electrical properties, adjusting a calibration curve, and/or making other adjustments. Calibration by calibration module 42 may be performed at predetermined intervals, with a predetermined frequency, based on user commands or inputs, based on performance of a measurement by intermittent assessment subsystem 14, and/or at other times.

Figure 2:
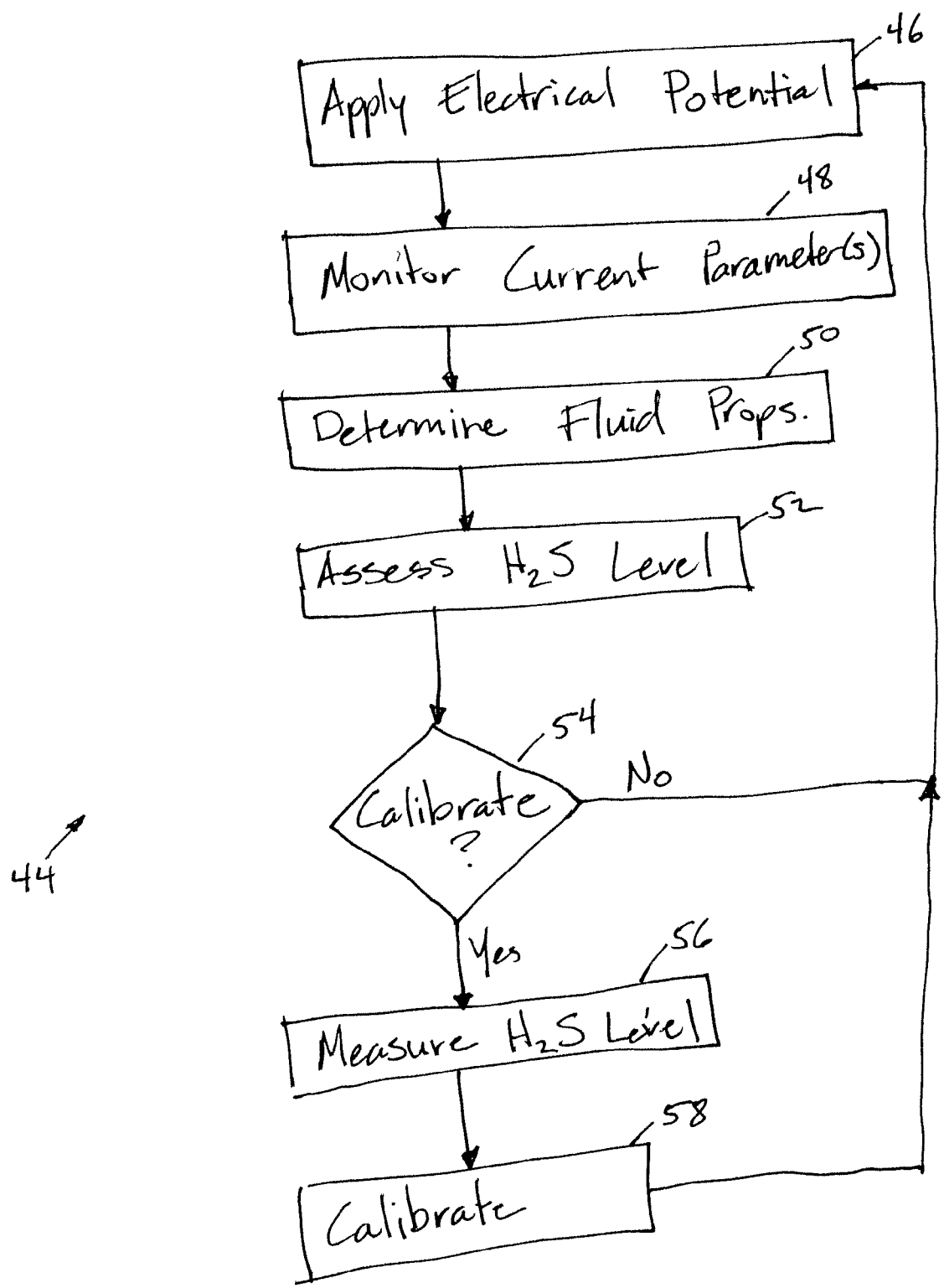
FIG. 2 illustrates a method of assessing the level of hydrogen sulfide in drilling fluid within a well, according to one or more embodiments of the invention.

FIG. 2 illustrates a method 44 of assessing the level of hydrogen sulfide in a well for removing hydrocarbons from the Earth in situ and/or in an ongoing manner. The operations of method 44 presented below are intended to be illustrative. In some embodiments, method 44 may be accomplished with one or more additional operations not described, and/or without one or more of the operations discussed. Additionally, the order in which the operations of method 44 are illustrated in FIG. 2 and described below is not intended to be limiting.

In some embodiments, method 44 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 44 in response to instructions stored electronically on an electronic storage medium. The one or more processing devices may include one or more devices configured through hardware, firmware, and/or software to be specifically designed for execution of one or more of the operations of method 44.

At an operation 46, an electric potential is applied between electrical conductors disposed in direct contact with drilling fluid in the well such that an electric current runs between the electrical conductors through the drilling fluid. In one embodiment, operation 46 is performed by a signal generator similar to or the same as signal generator 26 (shown in FIG. 1 and described above) under control of a generator control module similar to or the same as generator control module 34 (shown in FIG. 1 and described above).

At an operation 48, one or more parameters of the electric current induced within the drilling fluid are monitored. In one embodiment, operation 48 is performed by a sensor and/or current parameter module similar to or the same as sensor 28 and/or current parameter module 36, respectively (shown in FIG. 1 and described above).

At an operation 50, one or more electrical properties of the drilling fluid are determined. The determination is based on the one or more parameters of the electric current monitored at operation 48, one or more parameters of the potential applied at operation 46, and/or other parameters. The one or more properties may include one or more of reflectance, resistance, susceptibility, impedance, permittivity, admittance, real and imaginary terms, S-parameters, and/or other properties. In one embodiment, operation 50 is performed by a fluid property module similar to or the same as fluid property module 38 (shown in FIG. 1 and described above).

At an operation 52, an assessment of the level of hydrogen sulfide in the drilling fluid is made. Operation 52 may include presenting the assessment of the level of hydrogen sulfide to one or more users. The assessment of the level of hydrogen sulfide may be based on the one or more electrical properties determined at operation 50, one or more of the parameters monitored at operation 48, and/or other properties or parameters. In one embodiment, operation 52 is performed by a hydrogen sulfide concentration module similar to or the same as hydrogen sulfide concentration module 40 (shown in FIG. 1 and described above).

At an operation 54, a determination is made as to whether a calibration should be initiated. Calibration may be initiated periodically, at a predetermined or selected interval, based on user input or command, and/or at other times. If calibration is not initiated, method 44 returns to operation 46. If calibration is initiated, method 44 proceeds to an operation 56.

At operation 56, a separate measurement of the level of hydrogen sulfide in the drilling fluid. The measurement taken at operation 56 may be more reliable, precise, and/or accurate than the assessment made at operation 52. The measurement taken at operation 56 may be a direct and/or quantitative measurement of the level of hydrogen sulfide in the drilling fluid. The measurement may require extraction of drilling fluid from the well for testing. In one embodiment, operation 56 may be made by an intermittent assessment subsystem similar to or the same as similar to or the same as intermittent assessment subsystem 14 (shown in FIG. 1 and described above).

At operation 58, the level of hydrogen sulfide measured at operation 56 may be used to calibrate the assessment of the level of hydrogen sulfide at operation 52. This may include correlating the most recent measurement at operation 56 with a temporally corresponding assessment (or assessments) taken at operation 52. The calibration may take into account correlations of a plurality of past measurements taken at operation 56 (e.g., weighted according to timeliness) and corresponding measurements from operation 56. The calibration may result in an adjustment of future assessments of the level of hydrogen sulfide at operation 52. For example, the calibration may result in an adjustment to a threshold, an adjustment to a function that determines the level of hydrogen sulfide as a function of properties and/or parameters from operations 48 and/or 50, an adjustment to sensitivity to changes in one or more electrical properties, and/or other adjustments. In one embodiment, operation 58 is performed by a calibration module similar to or the same as calibration module 42.

While the above-described embodiments are generally directed to the ongoing, in situ monitoring of hydrogen sulfide gas in drilling fluid, it is also contemplated that other species of interest could similarly be monitored in the drill fluid—provided that the measured dielectric property values for another such system could be correlated with values and/or concentrations determined intermittently and/or calibratively, as described herein for drilling fluids comprising hydrogen sulfide. Examples of species of potential interest include, but are not limited to, CO, propane, butane, and the like.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A measurement system configured to assess hydrogen sulfide (H2S) concentration within drilling fluid, the drilling fluid being part of a drilling system configured to drill a wellbore in the Earth, the measurement system comprising:
   a) an intermittent assessment subsystem configured to quantitatively determine hydrogen sulfide concentration in the drilling fluid, wherein such determining is carried out on an intermittent basis; and
   b) an ongoing assessment subsystem configured to qualitatively assess changes in hydrogen sulfide concentration in the drilling fluid in situ and on an ongoing basis, the ongoing assessment subsystem comprising:
      i) electrical conductors in direct contact with drilling fluid within the drilling system;
      ii) a signal generator configured to apply an electric potential between the electrical conductors such that an electric current runs between the electrical conductors through the drilling fluid; and
      iii) a processor configured to measure an electrical property of the drilling fluid based on a parameter of the electric current, wherein values for the electrical property are a function of hydrogen sulfide concentration in the drilling fluid, and to assess changes in hydrogen sulfide concentration in the drilling fluid in situ based changes in the values for the electrical property over time, and
   wherein the ongoing assessment of changes in hydrogen sulfide concentration by the ongoing assessment subsystem is calibrated with the quantitative determination of hydrogen sulfide concentration provided intermittently by the intermittent assessment subsystem, so as to provide for a qualitative, in situ, continuous monitoring of hydrogen sulfide in the drilling fluid.

2. The measurement system of claim 1, wherein the signal generator is configured such that the electrical potential is an alternating current potential.

3. The measurement system of claim 2, wherein the alternating current potential is in a resonant frequency range determinable by dielectric spectroscopy.

4. The measurement system of claim 2, wherein the signal generator is configured such that the frequency of the alternating current potential is between about 50 MHz and about 80 MHz.

5. The measurement system of claim 1, wherein the signal generator is configured such that the amplitude of the potential is about 100 mV.

6. The measurement system of claim 1, wherein the electrical conductors comprise an inner conductor and an outer conductor of a coaxial conductor.

7. The measurement system of claim 1, wherein the processor is configured such that the electrical property includes one or more of reflectance, resistance, susceptibility, impedance, permittivity, admittance, real and imaginary terms, or S-parameters.

8. A method of assessing, in situ, hydrogen sulfide (H2S) concentration within drilling fluid in a drilling system configured to drill a wellbore in the Earth, the method comprising the steps of:
   a) applying an electric potential between electrical conductors disposed in direct contact with the drilling fluid in the drilling system such that an electric current runs between the electrical conductors through the drilling fluid;
   b) determining a value of an electrical property of the drilling fluid based on a parameter of the electric current running through the drilling fluid, wherein the value of the electrical property is a function of hydrogen sulfide concentration in the drilling fluid;
   c) quantitatively measuring hydrogen sulfide concentration in the drilling fluid;
   d) correlating the quantitative measurement with the value of the electrical property of the drilling fluid determined at (b);
   e) calibrating an assessment of hydrogen sulfide concentration in the drilling fluid that is based on determined values of the electrical property of the drilling fluid, wherein the calibration is based on the correlation performed at (d); and
   d) qualitatively assessing, in situ and on ongoing basis, hydrogen sulfide concentration in the drilling fluid based on ongoing determinations of the value of the electrical property of the drilling fluid.

9. The method of claim 8, wherein the electric potential is applied as an alternating current potential.

10. The method of claim 9, wherein the alternating current potential is in a resonant frequency range determined by dielectric spectroscopy.

11. The method of claim 10, wherein the frequency of the alternating current potential is between about 50 MHz and about 80 MHz.

12. The method of claim 11, wherein the amplitude of the electric potential is about 100 mV.

13. The method of claim 12, wherein substantial changes in one or more electrical properties triggers an automatic shut-off and containment of the drilling system.

14. The method of claim 8, wherein the one or more electrical properties comprise one or more of reflectance, resistance, susceptibility, impedance, permittivity, admittance, real and imaginary terms, or S-parameters.

* * * * *